(12) United States Patent
Dussaud et al.

(10) Patent No.: US 10,556,133 B2
(45) Date of Patent: Feb. 11, 2020

(54) COMPOSITION AND METHOD FOR STRENGTHENING HAIR FIBER

(71) Applicant: Momentive Performance Materials Inc., Waterford, NY (US)

(72) Inventors: Anne Dussaud, Tarrytown, NY (US); Bhavna Rana, White Plains, NY (US); Ronald Wagner, Bonn (DE); Kenrick M Lewis, Flushing, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 155 days.

(21) Appl. No.: 15/613,892

(22) Filed: Jun. 5, 2017

(65) Prior Publication Data

US 2018/0345048 A1    Dec. 6, 2018

(51) Int. Cl.

| | |
|---|---|
| *A61Q 5/00* | (2006.01) |
| *A61K 8/30* | (2006.01) |
| *A61K 8/19* | (2006.01) |
| *A61K 8/65* | (2006.01) |
| *A61K 8/37* | (2006.01) |
| *A61K 8/73* | (2006.01) |
| *A61K 8/365* | (2006.01) |
| *A61K 8/34* | (2006.01) |
| *A61Q 5/06* | (2006.01) |

(52) U.S. Cl.
CPC ............... *A61Q 5/002* (2013.01); *A61K 8/19* (2013.01); *A61K 8/30* (2013.01); *A61K 8/345* (2013.01); *A61K 8/365* (2013.01); *A61K 8/37* (2013.01); *A61K 8/65* (2013.01); *A61K 8/73* (2013.01); *A61Q 5/06* (2013.01); *A61K 2800/5426* (2013.01)

(58) Field of Classification Search
None
See application file for complete search history.

(56) References Cited

U.S. PATENT DOCUMENTS

| | | |
|---|---|---|
| 3,958,581 A | 5/1976 | Abegg et al. |
| 3,973,574 A | 8/1976 | Minagawa et al. |
| 4,614,200 A | 9/1986 | Hsiung et al. |
| 6,390,102 B1 | 5/2002 | Butts et al. |
| 6,475,568 B1 | 11/2002 | Czech |
| 6,506,371 B1 | 1/2003 | Butts et al. |
| 6,740,327 B2 | 5/2004 | Yu et al. |
| 7,713,310 B2 | 5/2010 | Lalleman |
| 8,802,066 B2 | 8/2014 | Fack et al. |
| 9,422,315 B2 | 8/2016 | Suenaga et al. |
| 2002/0119174 A1 | 8/2002 | Gardlik et al. |
| 2004/0261198 A1 | 12/2004 | Kainz et al. |
| 2011/0268681 A1 | 11/2011 | Gonzalez et al. |

FOREIGN PATENT DOCUMENTS

| | | | |
|---|---|---|---|
| CN | 101647766 A | 2/2010 | |
| FR | 2838051 A1 | 10/2003 | |
| KR | 100817669 A2 | 3/2008 | |
| WO | 0207700 A2 | 1/2002 | |
| WO | WO-2013167350 A2 * | 11/2013 | ............. A61K 8/365 |

OTHER PUBLICATIONS

Hair and Hair Care, Dale H. Johnson, ed., Marcel Dekker, Inc. (1997).
"Beginning Cosmetic Chemistry", 3rd ed., Angela Kozlowski ed., Alluredbooks (2009).
Dussaud et al., "Progressive hair straightening using an automated flat iron: Function of silicones". J. Cosmet. Sci., 64, 1-13 (Mar./Apr. 2013).
Yoder et al.: "The Synthesis and Analysis of Copper(II) Carboxylates", Journal of Chemical Education, 72(3): Mar. 1995, 267-269.
"Copolymer". Wikipedia dated Nov. 2016; pp. 1-7.
"Hair Iron". Wikipedia dated Jan. 25, 2016; pp. 1-3.
"Hair Straightening", Wikipedia dated Jan. 25, 2016, pp. 1-4.
U.S. Appl. No. 15/614,035.
U.S. Appl. No. 15/613,988.
"Utilisation de A CR paississant SEPIMAX ZEN pour prA CR parer des formulations cosma cr tiques pout 1 hygian et le sion"IP.com Journal, Jan. 10, 2012.
Database GNPD Online Mintel. Sep. 19, 2016.
International Search Report and Written Opinion dated Sep. 10, 2018.

* cited by examiner

*Primary Examiner* — Nannette Holloman
(74) *Attorney, Agent, or Firm* — Joseph S. Ostroff

(57) ABSTRACT

A hair fiber strengthening composition includes an aqueous vehicle containing as a hair strengthening additive a source of metal cations having a valence of 2 or 3 and anions derived from an oxidized carbohydrate, an inorganic acid and/or an organic acid, the composition having a pH of from about 6 to about 11.

24 Claims, No Drawings

COMPOSITION AND METHOD FOR STRENGTHENING HAIR FIBER

FIELD OF THE INVENTION

The present invention relates to a composition and method for strengthening hair fiber employing a particular source of metal cations as a hair strengthening agent.

BACKGROUND OF THE INVENTION

Compositions and methods for thermally shaping hair typically result in the degradation of one or more mechanical properties of the treated hair fibers, e.g., their strength, due to the use of harsh chemicals and/or the relatively high temperatures of the shaping methods themselves. The recent introduction of high temperature flat irons (T>150° C.) has encouraged the use of increasingly higher hair shaping temperatures. For example, high temperature ironing temperatures are utilized by hair salons in the thermal hair shaping method known as "Brazilian Blowout". This method consists of applying a hair treatment composition followed by a high temperature step employing a flat iron. When the hair treatment composition contains formaldehyde or formaldehyde precursor that releases formaldehyde at the ironing temperature, the crosslinking resulting from the reaction of the formaldehyde with hair keratin reduces or minimizes the heat-induced weakening of the treated hair fibers. The straightening quality and hair aesthetics obtained by application of the Brazilian Blowout method are clearly superior to those achieved by the use of conventional chemical hair relaxers. However, due to health concerns, the use of formaldehyde keratin crosslinkers is undergoing greater scrutiny and may become subject to regulatory restriction.

In contemplation of the reduction, if not discontinuance, of aldehydic keratin crosslinkers in hair treatment compositions and methods, whether induced voluntarily or by government regulation, there has arisen a need for a composition and method for the thermal shaping of hair that avoids or greatly limits the use of formaldehyde keratin crosslinkers but reduces or lessens the extent of damage to hair fibers, manifested as a reduction in the tensile strength of the thermally shaped hair fibers, in a manner that is at least as effective as the hair treatment compositions and thermal hair shaping methods they are intended to replace.

All thermal methods for the thermal shaping of hair result in some measurable reduction in tensile strength of the shaped hair fibers, the higher the hair shaping temperature generally accompanied by a correspondingly greater reduction in hair fiber strength.

There is thus a need for a hair fiber strengthening composition that will more effectively limit the extent of the reduction in hair fiber strength that accompanies the use of known and conventional thermal hair treatment compositions and methods such as Brazilian Blowout.

SUMMARY OF THE INVENTION

In accordance with the present invention, a hair fiber strengthening composition is provided which comprises an aqueous vehicle and a hair fiber strengthening agent which is at least one metal compound of the general formula:

$$Me^+(X^-)_n$$

wherein $Me^+$ is the cation of a metal having a valence equal to subscript n, subscript n is 2 or 3 and each $X^-$ independently is an anion of (i) an oxidized carbohydrate of the formula:

$$^-O-C(O)-R$$

wherein R is the residue of the same or different carbohydrate, or an anion (ii) derived from the same or different inorganic or organic acid, provided, there is at least one anion (i), the composition having a pH of from about 6 to about 11.

Further in accordance with the invention, there is provided a method for strengthening hair fiber which comprises:

a) contacting hair fiber to be strengthened with a hair fiber strengthening composition having a pH of from about 2 to about 12 prior to or on initial contact with the hair, the hair strengthening composition comprising a hair fiber strengthening agent in an aqueous vehicle, the hair strengthening agent being at least one metal compound of the general formula:

$$Me^+(X^-)_n$$

wherein $Me^+$ is the cation of a metal having a valence equal to subscript n, subscript n is 2 or 3, each $X^-$ independently is an anion of (i) an oxidized carbohydrate of the general formula:
wherein R is the residue of the same or different carbohydrate, or an anion (ii) derived from the same or different inorganic or organic acid; and, b) maintaining the hair fiber strengthening composition in contact with the fiber hair for a period of time sufficient to result in penetration of $Me^+$ cations into the cortex of the hair fiber and subsequent formation of hair fiber-strengthening chelate of $Me^+$ cations with cortex keratin thereof, provided, that where the hair fiber strengthening composition has a pH of from about 2 to less than about 6 at the time of or following penetration of $Me^+$ cations into the cortex of the hair fiber, the pH of the composition is adjusted to from about 6 to about 11 by the addition of base thereto.

The composition and method herein for the strengthening of hair fiber, typically carried out in conjunction with the thermal shaping of the hair, have been found to significantly lessen the sort of damage to thermally shaped hair fiber that often occurs as a result of the relatively harsh conditions of known and conventional thermal hair shaping procedures including, in particular, the aforementioned Brazilian Blowout method.

Treating hair to be thermally shaped with the foregoing hair fiber strengthening composition has been found to significantly lessen the degradation of one or more mechanical properties of the thermally shaped hair, e.g., hair fiber strength, compared with comparable hair that has not been treated with the hair strengthening composition herein.

While the mechanism by which the hair fiber strengthening agent herein mitigates damage to thermally shaped hair is currently not known with certainty and without wishing to be bound, it is believed that upon penetration of its metal cations into the cortex of the hair fiber, there subsequently forms a hair fiber strengthening chelate between the metal cations and keratinous protein(s) of the cortex.

The benefits realized from the method of thermally shaping hair in accordance with the invention are immediately apparent to professional hair stylists and their clients alike. Not only are any health issues associated with the use of aldehydes avoided, the resulting thermally shaped hair is noticeably more manageable and displays fewer breaks compared to hair lacking treatment by the method of this invention.

DETAILED DESCRIPTION OF THE INVENTION

Other than in the working examples, or where otherwise indicated, all numbers expressing amounts of materials, reaction conditions, time durations, quantified properties of materials, and so forth, stated in the specification and claims are to be understood as being modified in all instances by the term "about".

It will be understood that any numerical range recited herein includes all sub-ranges within that range and any combination of the various endpoints of such ranges or sub-ranges whether described in the examples or anywhere else in the specification.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "hair fiber" as used herein shall be understood to be synonymous with, and to include, "hair" per se, "hair fibers", "hair swatch(es)", "hair tress(es)" and terms and expressions of like import.

The term "shaping" as used herein shall be understood to apply to reshaping and, in particular, to straightening, hair.

The expression "color former" as used herein shall be understood to mean any organic compound or plant extract that is capable of reacting with the $Me^+$ cation of an $Me^+(X^+_n)$ hair fiber strengthening agent herein to produce color.

In addition to water, the hair fiber strengthening composition herein may contain one or more other components such as other salts, water-soluble and/or water miscible organic compounds such as alcohols, carboxylic acids and derivatives thereof, amines or other organic compounds, polymeric or oligomeric compounds such as polyols, polyamines and polyamidoamines, surfactants, emulsifiers, thickeners, dyes, organometallic compounds such as water-soluble organo silicon compounds or water-soluble transition metal compounds, and the like. Optionally, the hair fiber strengthening composition may contain water-wettable particles such as pigments, fillers, rheological additives, and the like.

A. HAIR FIBER STRENGTHENING AGENT

The hair fiber strengthening agent employed in the hair fiber strengthening composition and hair fiber strengthening method of the invention comprises as a source of metal ions at least one compound of the general formula $Me^+(X^-)_n$ wherein the metal cation $Me^+$ is one or more of $Fe^{2+}$, $Zn^{2+}$, $Mg^{2+}$, $Al^{3+}$, $Cu^{2+}$ and $Cu^{3+}$ cations.

Anions $X^-$ of the metal compound of formula $Me^+(X^-)_n$ are independently selected from those of oxidized carbohydrates and those derived from inorganic and organic acids.

(i) Anions of Oxidized Carbohydrate

In one embodiment of the hair fiber strengthening agent herein, at least one and up to three anions $X^-$ (when n=3) of metal compound $Me^+(X^-)_n$ is that of oxidized carbohydrate $^-O-C(O)-R$ as defined above. Thus, e.g., the hair fiber strengthening agent can be one or more metal compounds of the group:

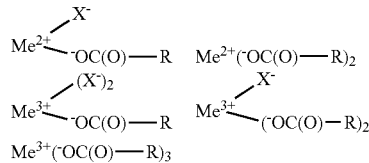

wherein $Me^{2+}$ and $Me^{3+}$ are metal cations having positive charges of 2 and 3, respectively, $X^-$ is the anion of an inorganic or organic acid and $^-OC(O)-R$ anion is that of oxidized carbohydrate as previously defined.

The oxidized carbohydrate may be used in either the dextro-rotary (D) or the levo-rotary (L) form and may be unsubstituted or substituted. When substituted, the oxidized carbohydrates useful herein may be amino-substituted, amido-substituted, phospho-substituted, or any mixture thereof.

The oxidized carbohydrates for use herein include substituted or unsubstituted monosaccharides, disaccharides, oligosaccharides, polysaccharides, and mixtures thereof. Suitable oxidized carbohydrates for use herein include, but are not limited to, oxidized aldoses, oxidized ketoses, oxidized trioses, oxidized tetroses, oxidized pentoses, oxidized hexoses, and mixtures thereof.

Specific examples of oxidized saccharides for use herein include, but are not limited to, ribonic acid; ribulonic acid; arabinonic acid; xylonic acid; xylulonic acid; lyxonic acid; allonic acid; altronic acid; gluconic acid; mannonic acid; gulonic acid; idonic acid; galactonic acid; talonic acid; glucoheptonic acid; psiconic acid; fructonic acid; sorbonic acid; tagatonic acid; lactobionic acid; maltobionic acid; isomaltobionic acid; cellobionic acid; oxidized malto-oligosaccharide; oxidized cello-oligosaccharide; oxidized cellulose; chitin; gum arabic; gum karaya; gum xanthan; oxidized gum guar; oxidized locust bean gum; oxidized agars; oxidized algins; and, oxidized gellan gum, pectins, hydrolyzed pectins and oxidized pectins.

Specific examples of oxidized disaccharides for use herein include, but are not limited to, lactobionic acid, maltobionic acid, isomaltobionic acid, cellobionic acid, oxidized malto-oligosaccharide, oxidized cello-oligosaccharide, and mixtures thereof.

Additional specific examples of oxidized polysaccharides for use herein include, but are not limited to, oxidized cellulose; chitin; gum arabic; gum karaya; gum xanthan; oxidized gum guar; oxidized locust bean gum; oxidized agars; oxidized algins; oxidized gellan gum, and mixtures thereof.

Specific examples of metal-containing complexes of oxidized carbohydrates for use herein include, but are not limited to, $Fe^{2+}$ lactobionate, $Fe^{2+}$ maltobionate, $Fe^{2+}$ isomaltobionate, $Fe^{3+}$ lactobionate, $Fe^{3+}$ maltobionate, $Fe^{3+}$ isomaltobionate, $Fe^{2+}$ gluconate, $Fe^{3+}$ gluconate, $Fe^{2+}$ glucoheptonate, $Fe^{3+}$ glucoheptonate, $Zn^{2+}$ lactobionate, $Zn^{2+}$ maltobionate, $Zn^{2+}$ isomaltobionate, $Zn^{2+}$ gluconate, $Zn^{2+}$ glucoheptonate, $Mg^{2+}$ maltobionate, $Mg^{2+}$ isomaltobionate, $Mg^{2+}$ gluconate, $Mg^{2+}$ glucoheptonate, $Al^{3+}$ maltobionate, $Al^{3+}$ isomaltobionate, $Al^{3+}$ gluconate, glucoheptonate, $Cu^{2+}$ maltobionate, isomaltobionate, $Cu^{2+}$ gluconate, glucoheptonate, $Cu^{3+}$ maltobionate, $Cu^{3+}$ isomaltobionate, $Cu^{3+}$ gluconate, $Cu^{3+}$ glucoheptonate, and mixtures thereof.

$Zn^{+2}$ lactobionate may, e.g., be represented by the following structure:

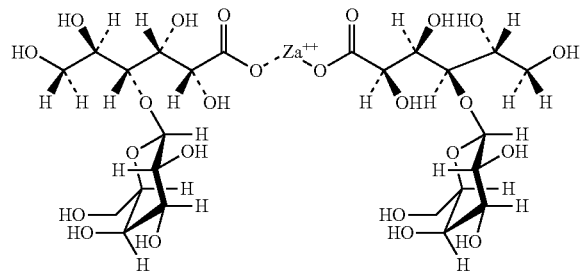

Specific examples of hair fiber strengthening metal compounds $Me^+(X^-)_n$ wherein at least one $X^-$ is the anion of an inorganic/organic acid and the remaining anion or anions are those of oxidized carbohydrate include $Fe^{2+}$ chloride lactobionate, $Fe^{2+}$ chloride lactobionate, $Fe^{2+}$ sulfate lactobionate, $Fe^{2+}$ acetate lactobionate, $Fe^{3+}$ chloride maltobionate, $Fe^{3+}$ sulfate maltobionate, $Fe^{3+}$ acetate maltobionate, $Zn^{+2}$+ chloride lactobionate, $Zn^{+2}$ sulfate lactobionate, $Zn^{3+}$ chloride maltobionate, $Zn^{3+}$ acetate maltobionate, and the like and mixtures thereof.

It is essential for the stability of the hair fiber strengthening composition herein that the mole ratio of $^-O$—C(O)—R anion(s) to $Me^+$ cation(s) of the hair fiber strengthening agent be greater than about 1.0, e.g., 1.2, 1.3, etc. In one embodiment of the invention, the mole ratio of $^-O$—C(O)R anions to $Me^+$ cation(s) can range from above about 1.0 to about 2.0 and advantageously from about 1.2 to about 1.8. At or below a mole ratio of 1.0, hair treating compositions containing a $Me^+(^-O$—C(O)—R)$_n$ compound may separate into two phases, such being an indication of the instability of the compositions and consequently their unsuitability for use as hair strengthening compositions and in hair fiber strengthening treatment methods.

In the hair fiber strengthening composition of the invention, the mole concentration of $Me^+$ cations therein advantageously ranges from about 0.01 to about 2, preferably from about 0.1 to about 1.0 and more preferably from about 0.2 to about 0.5.

(ii) Anions Derived from Inorganic/Organic Acids

In another embodiment of the hair fiber strengthening agent herein, each anion $X^-$ of metal compound $Me^+(X^-)_n$ is independently that of an organic or inorganic acid, e.g., chloride, fluoride, sulfate, alkysulfonate, arysulfonate, alkarylsulfonate, phosphate, oxalate, acetate, citrate, lactate, etc., anion. Specific examples of such metal compounds include $Fe^{2+}$ chloride, $Fe^{2+}$ fluoride, $Mg^{+2}$ chloride, $Fe^{3+}$ chloride, $Fe^{2+}$ sulfate, $Fe^{2+}$ sulfate, $Mg^{+2}$ sulfate, $Fe^{2+}$ phosphate, $Fe^{3+}$ phosphate, $Mg^{+2}$ phosphate, $Fe^{2+}$ oxalate, $Fe^{3+}$ oxalate, $Fe^{2+}$ acetate, $Fe^{3+}$ acetate, $Fe^{2+}$ glycerophosphate, $Fe^{2+}$ glycerophosphate, $Zn^{2+}$ chloride, $Zn^{2+}$ fluoride, $Zn^{2+}$ sulfate, $Zn^{2+}$ phosphate, $Zn^{2+}$ acetate, $Zn^{2+}$ aspartate, $Zn^{2+}$ citrate, $Zn^{2+}$ lactate, $Zn^{2+}$ malate, $Zn^{2+}$ glycerophosphate, $Fe^{2+}$ glycinate, $Mg^{2+}$ aspartate, $Mg^{2+}$ citrate nonahydrate, $Mg^{2+}$ gluconate, $Mg^{+2}$ lactate, $Mg^{+2}$ glycerophosphate, $Mg^{+2}$ malate, $Mg^{2+}$ glycinate, $Al^{3+}$ sulfate, $Al^{3+}$ chloride and $Cu^{2+}$ sulfate. These salts can be anhydrous or hydrated such as the monohydrates, trihyhydrates, pentahydrates, hexahrydates, heptahydrates, nonahydrate, and the like.

(iii) Mixtures of Anions (i) and (ii).

It is also within the scope of the invention to utilize a mixture of metal compounds $Me(X^-)_n$, e.g., a mixture (iii) of at least one metal compound (i) wherein $X^-$ is the anion of an oxidized carbohydrate, and at least one metal compound (ii) wherein $X^-$ is the anion of an inorganic or organic acid. Illustrative of mixtures (iii) of anions (i) and (ii) are those containing at least one metal compound (i) selected from the group consisting of $Fe^{2+}$ lactobionate, $Fe^{2+}$ maltobionate, $Fe^{2+}$ isomaltobionate, $Fe^{3+}$ lactobionate, $Fe^{3+}$ maltobionate, $Fe^{3+}$ isomaltobionate, $Fe^{2+}$ gluconate, $Fe^{3+}$ gluconate, $Fe^{2+}$ glucoheptonate, $Fe^{2+}$ glucoheptonate, $Zn^{2+}$ lactobionate, $Zn^{2+}$ maltobionate, $Zn^{3+}$ isomaltobionate, $Zn^{2+}$ gluconate, $Zn^{2+}$ glucoheptonate, $Zn^{2+}$ glycerophosphate, $Mg^{2+}$ maltobionate, $Mg^{2+}$ isomaltobionate, $Mg^{2+}$ gluconate, $Mg^{2+}$ glucoheptonate, $Al^{3+}$ maltobionate, $Al^{3+}$ isomaltobionate, $Al^{3+}$ gluconate, $Al^{3+}$ glucoheptonate, $Cu^{2+}$ maltobionate, $Cu^{2+}$ isomaltobionate, $Cu^{2+}$ gluconate, $Cu^{2+}$ glucoheptonate, $Cu^{2+}$ maltobionate, $Cu^{2+}$ isomaltobionate, $Cu^{3+}$ gluconate and $Cu^{3+}$ glucoheptonate and at least one metal compound (ii) selected from the group consisting of $Fe^{2+}$ chloride, $Fe^{3+}$ chloride, $Fe^{2+}$ sulfate, $Fe^{3+}$ sulfate, $Fe^{2+}$ phosphate, $Fe^{3+}$ phosphate, $Fe^{2+}$ glycerophosphate, $Fe^{3+}$ glycerophosphate, $Fe^{2+}$ oxalate, $Fe^{3+}$ oxalate, $Fe^{2+}$ acetate, $Fe^{3+}$ acetate, $Zn^{+2}$ chloride, $Zn^{+2}$ sulfate, $Zn^{+2}$ phosphate, $Zn^{+2}$ glycerophosphate, $Zn^{+2}$ acetate, $Mg^{2+}$ sulfate, $Al^{3+}$ chloride, $Al^{3+}$ sulfate, $Al^{3+}$ phosphate, $Cu^{2+}$ chloride, $Cu^{3+}$ chloride, $Cu^{2+}$ sulfate, $Cu^{3+}$ sulfate, $Cu^{2+}$ phosphate and $Cu^{3+}$ phosphate.

Where a hair fiber strengthening agent contains at least one compound $Me^+(X^-)_n$ containing both inorganic/organic acid-derived anion(s) and oxidized carbohydrate anion(s) and/or a mixture of metal compounds $Me^+(X^-)_n$ at least one of which contains inorganic/organic acid-derived anion(s) and at least one of which contains oxidized carbohydrate anion(s), it may be desirable to provide a molar ratio of $^-O$—(CO)—R anion to inorganic/organic acid anion(s) of from about 0.1 to about 15 and preferably from about 0.5 to about 5.

B. AQUEOUS VEHICLE

The aqueous vehicle for the hair fiber strengthening agent can be water, a dispersion (emulsion), e.g., of the oil in water (O/W) or water in oil (W/O) type, in which the hair fiber strengthening agent is dissolved in the aqueous phase. Suitable aqueous vehicles and their preparation are well known in the personal care and cosmetic arts, e.g., "Hair and Hair Care", Dale H. Johnson, ed., Marcel Dekker, Inc. (1997), and "Beginning Cosmetic Chemistry", 3$^{rd}$ ed., Angela Kozlowski ed., Alluredbooks (2009), the entire contents of which are incorporated by reference herein.

The hair fiber strengthening composition will contain at least a hair strengthening amount of hair strengthening $Me^+(X^-)_n$ compound dissolved in the aqueous component thereof. In general, such amounts can vary from about 0.1 to about 80 weight percent in one embodiment, from about 1 to about 60 weight percent in another embodiment and from 5 to about 40 weight percent in yet another embodiment, based on the total weight of the hair strengthening composition.

In one embodiment, the hair fiber strengthening composition herein will contain relatively little, if any, formaldehyde, for example, less than about 5, preferably less than about 1 and more preferably less than about 0.1, weight percent formaldehyde. This absence of formaldehyde represents a significant departure from hair fiber treatment compositions employed in the Brazilian Blowout method where up to 20 weight percent formaldehyde is commonly present.

It is essential that the hair strengthening, composition herein have, or be adjusted to have, a pH of from about 6 to about 11, in a preferred embodiment a pH of from about 7 to about 10 and in a more preferred embodiment a pH of from about 8 to about 9, at the time of or following penetration of $Me^+$ cations into the cortex of the hair fibers, e.g., from about 0 to about 30, preferably from about 1 to about 10, and more preferably from about 2 to about 5, minutes after initial contact of the hair strengthening composition with the hair to be strengthened. Below about pH 6, compositions containing an $Me^+(X^-)_n$ compound have been found to be ineffective due, it is thought, to the inability of the $Me^+$ cations to form a hair strengthening chelate with hair keratin protein at these pH levels, and above a pH of about 11 such compositions are undesirable for being excessively caustic. Thus, e.g., where the pH of a composition containing an $Me^+(X^-)_n$ compound has a pH of from about 2 to less than about 6 at or following the time of its having penetrated the cortex of the hair fibers, in order to effectively function as a hair strengthening composition, its pH must be adjusted in situ to within the range of from about 6 to about 11 in order for the aforesaid hair strengthening chelate to form.

Provided the hair strengthening composition remains stable at a pH of from about 2 to about 12, it can be adjusted to within this pH range at the time of its preparation and stored until needed for application. In general, hair strengthening compositions herein in which at least one $X^-$ anion is $^-O-C(O)-R$ tend to be storage stable at a pH of from about 6 to about 11. However, it may be the case that a specific composition containing a hair strengthening additive $M^+(X^-)_n$ in which two, and particularly three, $X^-$ anions are derived from an organic or inorganic acid are storage stable only within the range of from 2 to less than about 6, i.e., are stable only under strongly to mildly acidic conditions, and above about pH 6, are unstable as manifested by phase separation. When such instability is experimentally determined to be the case, adjustment of pH to within the range of from about 6 to about 11 may be deferred to or about the time the hair strengthening composition is applied to hair to be treated, such pH adjustment thereby allowing the formation of hair fiber strengthening chelate to proceed. Formation of the hair fiber strengthening chelate takes place fairly rapidly within the aforestated pH range of from about 6 to about 12, e.g., on the order of from about 30 seconds to about 30 minutes and typically within 5 to about 15 minutes.

In almost all cases, the hair fiber strengthening method of the invention will be accompanied or followed by thermal hair shaping, e.g., a hair straightening method such as any of the heretofore conventional or otherwise known hair straightening methods. Thermal hair relaxing refers to thermal hair shaping that is wash resistant and usually implies an the like, the use of which are well known in the art. Thermal hair shaping can be performed on damp or dry hair. Providing moisture, e.g., an aqueous mist or steam, can assist or facilitate the hair shaping procedure. Irons capable of generating steam or delivering ultrasonic aqueous mists are known for this purpose.

In view of the foregoing, whether prepared prior to storage or just prior to application, e.g., in situ, the hair fiber strengthening composition herein at or about the time of its penetration into the cortex of the hair fibers must have a pH of from about 6 to about 11. Suitable bases for achieving the aforesaid pH range include the hydroxides as well as the carbonates, bicarbonates, phosphates and borate salts of various alkali and alkali earth metals such as potassium, sodium, lithium or calcium, respectively. Preferred representatives thereof are in particular sodium carbonate, sodium bicarbonate, sodium phosphate, sodium borate, and mixtures thereof. Also suitable as pH adjusting bases are the aminosilanes and aminosilicones. Further suitable pH adjusting agents include primary, secondary and tertiary amines suitable representatives of which include monoethanol amine (MEA), 2-amino-2-methyl-propanol (AMP), 2-butylethanol amine (BEA), triethanolamine (TEA), N,N-dimethylethanolamine (DMEA), tromethamine, arginine, lysine, and N,N-bis(2-hydroxyethyl)glysine, glucosamine, N-methylglucamine.N-octylglucosamine, and mixtures thereof.

Where pH adjustment is carried out by hair salon personnel, packets of basic solutions predetermined to effect pH adjustment to within the necessary range when combined with a particular hair strengthening composition can be provided for this purpose.

C. OPTIONAL COMPONENTS

In addition to its hair fiber strengthening additive, the hair fiber strengthening composition herein can contain one or more optional components that enhance its functionality and/or facilitate its application, e.g., when the composition is intended to additionally function as a thermal hair shaping composition.

Table I below lists representative optional components for addition to the hair fiber strengthening composition of the invention in the indicated amounts:

TABLE I

| | Optional Components (Wt %) | | | |
|---|---|---|---|---|
| Optional Component | First Embodiment | Second Embodiment | Third Embodiment | Fourth Embodiment |
| Silicone-Based Hair Conditioning Agents (i) | 0.05 to 30 | 0.5 to 30 | 1 to 30 | 1 to 20 |
| Organic Diluents/Solvents (ii) | 2 to 99.95 | 10 to 99.95 | 20 to 99 | 30 to 99 |
| Surfactants/Emulsifiers (iii) | up to 15 | up to 10 | up to 5 | — |
| Viscosity Modifiers (iv) | 0.01 to 10 | — | — | — |
| Emollients, Fatty Substances (v) | up to 15 | up to 10 | up to 5 | — |
| Preservatives (vi) | 0.1 to 5 | 0.3 to 3 | 0. | 0.05 to 15 |
| Skin Protectants (vii) | 0.1 to 10 | 0.5 to 5 | — | — |
| Penetration Enhancers (viii) | 0.05 to 5 | 0.1 to 3 | — | — |
| Antioxidants (ix) | 0.01 to 5 | 0.1 to 3 | — | — |
| $M^+$ Cation-Reactive Color Formers (x) | 0.1 to 10 | 0.5 to 5 | — | — |
| Auxiliary Agents (xi) | up to 20 | 0.5 to 10 | 1 to 10 | — | ironing temperature from about 130° to about 250° C., and preferably from about 180° to about 230° C.

Thermal hair shaping methods involve the shaping of hair by application of heat provided, e.g., by a flat iron, curling iron, hot comb, hot rollers, microwave-heated curlers, and Silicone- and Silicone-Based Hair Conditioning Agents (i)

Among the useful hair conditioning agents that can be used herein are the polydimethysilicones ranging in viscosity from about 10 to about 1 million mPas, $C_2$-$C_{18}$ alkylderivatized silicones, dimethiconols, polyether-modified silicones, silicones containing amino groups and/or quaternized ammonium groups, and the like, and mixtures thereof. Preferred silicones are dimethiconol or dimethicone emulsions such as Silsoft EMU121-N and Silsoft EMU160-A emulsions available from Momentive Performance Materials Inc., and Xiameter MEM-1784 and Xiameter HMW2220 silicone emulsions available from Dow Corning Suitable aminosilicone-based hair conditioning agents are those containing primary, secondary and/or tertiary amino groups, e.g., aminopropyl-substituted and aminoethylaminopropyl-substituted silicones, aminosilicones obtained from the reaction of epoxysilicones with primary and secondary amines such as methylamine, propylamines, butylamine, ethanolamine, glucamine, dimethylamine, diethylamine, diethanolamine, morpholine, N,N-dimethylpropylenediamine, N-methylpiperazine, N-methylglucamine, and the like. Commercially available aminosilanes and aminosilicones include Silsoft A1100 aminosilane, SF 1708 amine silicone fluid, Silsoft AX alkyl-modified amino fluid and SME 253 aminosilicone-based emulsion, all from Momentive Performance Materials Inc.

Suitable quaternary ammonium group-containing conditioning agents are a,co-quat group-terminated silicones, quat group-terminated T-shaped silicones, a,co-silicone block-terminated quats and silicone-containing quat groups in comb-like configurations and optionally containing additional moieties such as polyethers and/or aromatic structures. Commercially available quaternary ammonium-containing silicone conditioning agents include Silsoft Silk, Silsoft A+ and Silsoft CLX-E silicone conditioning agents, Magnasoft SilQ and TP3877 silicones, all available from Momentive Performance Materials Inc.

Other suitable quat group-containing silicones are the quat group/silicone block-based copolymers, quat group/silicone block/hydrophilic block-based copolymers such as those having terminal monofunctional silicone moieties and quat group-terminated silicones bearing pendant amino groups.

Still other suitable silicone-based conditioning agents are the silicone betaines.

It is, of course, within the scope of the invention to use any of the known non-silicone hair conditioning agents in place of part or all of the foregoing silicone-based hair conditioners. Illustrative of such hair conditioning agents are cetyl trimethyl ammonium chloride, steardimonium chloride, dipalmitoyl dimonium chloride, distearyl dimethyl ammonium chloride, stearamidopropyl trimonium chloride, behenotrimonium chloride, behenamidopropyl ethyldimonium ethosulfate, dioleolethyl dimethyl ammonium methosulfate, dioleoylethyl hydroxyethylmonium methosulfate, and stearamidopropyl dimethylamine, behenamidopropyl dimethylamine. Other useful hair conditioning agents include polyquaternium-7, quaternium-8, polyquaternium-10, quaternium-14, quaternium-15, quaternium-18, quaternium-22, quaternium-24, quaternium-26, quaternium-27, quaternium-30, quaternium-33, quaternium-37, quaternium-53, quaternium-60, quaternium-61, quaternium-72, quaternium-78, quaternium-80, quaternium-81, quaternium-82, quaternium-83, quaternium-84, quaternium-91, cationic guars such as Jaguar 16 S available from Solvay Novecare, and cationic celluloses.

As previously indicated, the hair fiber strengthening method of the invention will ordinarily be carried out in conjunction with a thermal hair shaping procedure such as that illustrated below in certain of the examples. One or more conditioning agents may optionally be included in the hair fiber strengthening composition in order to facilitate the ironing step of the thermal hair shaping procedure and improve shaping and hair manageability. The conditioning agents can be organic polymers, cationic polymers, cationic surfactants, waxes, oils or silicones. The silicone polymers can be linear polymers, branched or crosslinked, block copolymers or comb copolymers. They can contain organic functional groups such as acid groups (carboxylic, sulfonate, phosphate), amine groups, polyether groups, polyglycerol groups, hydroxyl groups, carbohydrate groups or other polar groups. The silicone treatment can be a blend of several silicones, e.g., a blend of silicone resins and linear silicones. The silicones can be in the form of an emulsion or can be dissolved in an apolar diluent. The silicone can contain reactive groups such as silyl groups, methylol groups, aldehyde groups, azetidine groups, thiol groups, vinyl groups, catechol groups, galloyl groups, or the like.

Preferred optional conditioning and ironing aid silicones are anionic silicones containing acidic groups such as Silform INX carboxylated silicone available from Momentive Performance Materials Inc.

Organic Diluents/Solvents (ii)

Examples of cosmetically acceptable organic diluents/solvents include hydrocarbons of varying viscosities, e.g., linear and/or branched $C_5$ to $C_{20}$ hydrocarbons such as isododecane and petroleum jelly, mono-, di-, tri- and higher alcohols, e.g., ethanol, 1-propanol, 2-propanol, t-butanol, 2-methyl-1,3-propanediol and the ethers and esters thereof, in particular, mono-$C_1$-$C_4$-alkyl ethers, 1-methoxypropanol, 1-ethoxypropanol, ethoxydiglycol and their esters, 1,3- and 1,4-butanediol, pentylene glycol, hexylene glycol, diethyleneglycol and the monomethyl, monoethyl and monobutyl ethers and esters thereof, dipropylene glycol and the monomethyl, monoethyl and monobutyl ethers and the esters thereof, glycerol, diglycerol, hexanetriol, sorbitol, ethyl carbitol, benzyl alcohol, benzyloxy ethanol and the ethers or esters thereof, e.g., glycerol mono-, di- and triesters such as sweet almond oil and sunflower oil, fatty acid esters such as isopropyl myristate, isopropylpalmitate, oleyl oleate, decyl oleate, myristyl myristate and cetearyl ethylhehanoate, ethers such as di-n-octyl ether and bis-(2-ethyl-hexyl)ether such as oligoglycols, i.e. tripropylene glycol, carbonates such as propylene carbonate and pyrrolidones such as the N-alkyl pyrrolidones, propanediol, caprylyl glycol and ethylhexylglycerin.

The hair fiber strengthening composition herein preferably contains organic diluent/solvent in an amount of from 0 to about 70, preferably from 0 to about 50, and more preferably from about 2 to about 50 weight percent by total weight of the composition.

Generally, the addition of organic diluent/solvent improves the homogeneity of the hair fiber strengthening composition herein and its penetration into hair fiber to be strengthened.

Surfactants/Emulsifiers (iii)

The hair fiber strengthening composition herein may contain at least one surfactant/emulsifier selected from among the silicone-based and hydrocarbon-based surfactant/emulsifiers having an HLB value ranging from about 1 to about 20, preferably from about 1 to about 7 and more preferably from about 1 to about 5, weight percent of the entire composition.

In one embodiment of the hair fiber strengthening composition herein, such composition is formulated as a W/O formulation while in another embodiment, the hair fiber strengthening composition is formulated as an O/W formulation.

Examples of suitable surfactants/emulsifiers include anionic, nonionic, cationic, betaine and amphoteric silicone-based surfactants/emulsifiers.

Suitable examples of nonionic surfactants/emulsifiers include ethylene oxide (HO), propylene oxide (PO) and butylene oxide (BO)-containing linear or branched $C_8$ to $C_{50}$, preferably $C_8$-$C_{40}$ and more preferably $C_8$-$C_{24}$ fatty alcohols and fatty acid surfactants/emulsifiers as well as saccharide-based compounds such as the alkyl glucosides, alkoxylated fatty acid sorbinate esters, fatty acid glucamides, semi-polar amine oxides, phosphine oxides, sulfoxides, saturated or unsaturated alcohol ethoxylates having $C_{10}$-$C_{15}$ alkyl chains and from about 5 to about 80 EO units, linear or branched alcohol ethoxylates having $C_{11}$-$C_{17}$ alcohol chains and from about 5 to about 100 EO units, saturated or unsaturated ethoxylates-propoxylates having $C_{10}$-$C_{18}$ carbon chains and from about 2 to about 20 EO units, ethoxylate-propoxylates containing from about 5 to about 70 weight percent EO units, saturated or unsaturated fatty acid-based ethoxylates having $C_{10}$-$C_{18}$ carbon chains and from about 5 to about 100 EO units, saturated or unsaturated fatty acid-based castor oil ethoxylates having $C_{10}$-$C_{18}$ alkyl chains and from about 5 to about 80 EO units, saturated or unsaturated fatty acid-derivative oligoglycerines examples of which include fatty acid-derivatized di, tri and tetraglycerines such as the mono- or diester diglycerines having $C_{10}$-$C_{18}$ alkyl chains and from about 5 to about 100 EO units, saturated or unsaturated fatty acid sorbitane ester-based ethoxylates having $C_{10}$-$C_{18}$ alkyl chains and from about 50 to about 80 EO units attached to the sorbitane ring, saturated or unsaturated alcohol-based glycosides having $C_8$-$C_{18}$ alkyl chains and from 1 to about 10 glycosyl units, saturated or unsaturated fatty acid-based glucamides such as N-methylglucamides having $C_8$-$C_{18}$ alkyl chains, saturated or unsaturated fatty acid-based alkanolamides having $C_8$-$C_{12}$ alkyl chains, fatty amine and fatty acid amide-based amineoxides having $C_8$-$C_{30}$ alkyl chains, saturated or unsaturated fatty alcohol-based polyether sulfates having $C_{10}$-$C_{18}$ alkyl chains and from about 2 to about 30 EO units, and saturated or unsaturated fatty alcohol-based polyether carboxylates having $C_8$-$C_{18}$ alkyl chains and from about 2 to about 30 EO units.

Suitable anionic surfactants/emulsifiers include those containing carboxylate, sulfate, sulfonate, phosphate and/or phosphonate groups such as the linear or branched $C_8$-$C_{50}$, preferably $C_8$-$C_{40}$, more preferably $C_8$-$C_{24}$ alkyl, fatty alcohol and fatty acid-based groups, e.g., $C_8$-$C_{24}$ fatty acid carboxylates, $C_8$-$C_{24}$ fatty acid polyether carboxylates, $C_8$-$C_{24}$ fatty acid polyether sulfates, $C_8$-$C_{24}$ maleic acid addition products, $C_8$-$C_{24}$ fatty alcohol sulfates, $C_8$-$C_{24}$ sulfonates, and $C_8$-$C_{40}$ phosphates containing one or two fatty acid moieties.

Suitable cationic emulsifiers include those containing quaternary ammonium groups with $C_8$-$C_{50}$, preferably $C_8$-$C_{40}$ and more preferably $C_8$-$C_{30}$ alkyl, fatty alcohol and fatty acids, e.g., fatty acid based ester quats containing one or two fatty acid moieties, fatty amines and ethoxylated/propoxylated fatty amines.

Preferably, the cationic surfactant is a mono-long alkyl, -tri short alkyl quaternized ammonium salt or di-long alkyl, -di short alkyl quaternized ammonium salt wherein one or two alkyl substituents are selected from $C_8$-$C_{30}$ aliphatic groups or aromatic, alkoxy, polyoxyalkylene, alkylamido, hydroxyalkyl, aryl or alkylaryl groups having up to about 30 carbon atoms, the other alkyl groups being independently selected from $C_1$-$C_8$ aliphatic groups or aromatic, alkoxy, polyoxyalkylene, alkylamido, hydroxyalkyl, aryl or alkylaryl groups having up to about 8 carbon atoms wherein the counter ion is a salt-forming anion such as those selected from halogen (e.g., chloride, bromide), acetate, citrate, lactate, glycolate, phosphate, nitrate, sulfonate, sulfate, alkylsulfate, glutamate and alkyl sulfonate radicals. The aliphatic groups can contain, in addition to carbon and hydrogen atoms, ether linkages, and other groups such as amino groups. The longer chain aliphatic groups, e.g., those of about 8 carbons or higher, can be saturated or unsaturated. Preferably, one alkyl group is selected to be an alkyl group of from about 8 to about 30 carbon atoms, more preferably from about 14 to about 26 carbon atoms and still more preferably from about 14 to 22 carbon atoms; the other alkyl groups being independently selected from the group consisting of methyl, ethyl, propyl, isopropyl, butyl, isobutyl, etc., and mixtures thereof with the counter ion being selected from the group consisting of Cl—, Br—, $CH_3OSO_{3-}$, and mixtures thereof. It is believed that such mono-long alkyl quaternized ammonium salts can provide, in addition to their emulsification capability, improved slippery and slick feel on wet hair compared to multi-long alkyl quaternized ammonium salts. It is also believed that mono-long alkyl quaternized ammonium salts can provide improved hydrophobicity and smooth feel on dry hair compared to amine or amine salt cationic surfactants.

Nonlimiting examples of such mono-long alkyl quaternized ammonium salt cationic surfactants include: behenyl trimethyl ammonium chloride, stearyl trimethyl ammonium chloride, cetyl trimethyl ammonium chloride, behenyltrimethylammonium methyl sulfate, hydrogenated tallow alkyl trimethyl ammonium chloride, stearyl dimethyl benzyl ammonium chloride, and stearoyl amidopropyl dimethyl benzyl ammonium chloride. Preferred cationic surfactants are saturated or unsaturated fatty acid based mono-ester and di-ester quats having $C_{10}$-$C_{18}$ alkyl chains.

Suitable betaine surfactants/emulsifiers include those containing carbobetaine, sulfobetaine, phosphatobetaine and phosphonatobetaine groups with linear or branched $C_8$-$C_{50}$, preferably $C_8$-$C_{40}$, more preferably $C_8$-$C_{30}$ alkyl, fatty alcohol and fatty acid based groups such as the cocoamidopropyl carbobetaines.

In general, betaine surfactants such as those heretofore known for use in shampoo or other personal care products are suitable for use herein. These betaine surfactants include those broadly described as derivatives of aliphatic secondary and tertiary amines in which the aliphatic radical can be straight or branched chain and wherein one of the aliphatic substituents contains from about 8 to about 30 carbon atoms and one contains an anionic group such as a carboxy, sulfonate, sulfate, phosphate or phosphonate group. Suitable betaine surfactants/emulsifiers include those broadly described as derivatives of aliphatic quaternaryammonium, phosphonium, and sulfonium compounds in which the aliphatic radicals can be straight or branched chain, and wherein one of the aliphatic substituents contains from about 8 to about 30 carbon atoms and one contains an anionic group such as carboxy, sulfonate, sulfate, phosphate or phosphonate. Preferred carbobetaine surfactants are saturated or unsaturated fatty acid-based sarcosides having $C_{10}$-$C_{18}$ alkyl chains, saturated or unsaturated fatty acid-based amido propyl betaines having $C_{10}$-$C_{18}$ alkyl chains, and saturated or unsaturated fatty acid based taurides having $C_{10}$-$C_{18}$ alkyl chains.

Suitable amphoteric surfactants for use in the formulations of the present invention include cocoamphoacetate, cocoamphodiacetate, lauroamphoacetate, lauroamphodiacetate, and mixtures thereof.

Preferred examples of silicone-based nonionic emulsifiers are ethylene oxide (EO), propylene oxide (PO) and butylene oxide (BO)-containing emulsifiers of the ABA type with EO/PO/BO moieties attached to the terminal ends of a silicone chain or emulsifiers having polyether moieties attached to the silicone chain in a comb-like arrangement, e.g., SF 1540 silicone available from Momentive Performance Materials Inc. In one embodiment, hydrophilic polyether moieties as well as oleophilic alkyl chains are attached to the silicone chain. In another embodiment, hydrophilic polyglycerol moieties as well as alkyl or fatty alcohol ether/fatty acid ester moieties are attached to the silicone chain. In yet another embodiment, amodimethicone glycerocarbamates are used. In still another embodiment of the invention, cetyl diglyceryl tris(trismethylsiloxy)silyl-ethyl dimethicones are employed. The latter four types of silicone emulsifiers are especially preferred for W/O emulsions.

Preferred examples for cationic silicone emulsifiers are quaternary ammonium group- or amino group-containing emulsifiers of the ABA type with EO/PO moieties attached to the terminal quat or amino ends of a silicone chain or quat/amino emulsifiers having polyether moieties attached to the silicone chain in a comb-like arrangement.

In another embodiment, hydrophilic polyhydroxy moieties as well as oleophilic fatty alkyl or fatty alkyl ester moieties are attached to the silicone chain, e.g., Silform EOF silicone available from Momentive Performance Materials Inc.

Viscosity Modifiers (iv)

Optional viscosity modifying agents for use in the hair strengthening composition herein may be any agent capable of modifying the viscosity, thickness or rheology properties of such composition, in particular gelling agents and thickening agents.

The viscosity modifying agent may be selected, in particular, from gelling agents in polymeric or organic form, and gelling agents in mineral or inorganic form. Examples of useful polymers include cationically or anionically substituted celluloses. Examples of suitable polymeric thickeners include polysaccharides such as xanthan gum, guar, carrageenan gum and gellan, gelatin, starches and synthetic polymers such as polyacrylamide polymers and polyacrylate thickeners (carbomers). Examples of organic gelling agents include silicone gums, polyurethanes and liquid fatty phase gelling agents. Suitable inorganic gelling agents include clays such as tetraalkylammonium-modified clays, and silicas including hydrophobically-modified silicas and magnesium aluminum silicates. Viscosity can be also be modified with fatty materials, e.g., fatty alcohols such as cetyl alcohol and stearyl alcohol, ethoxylated waxes (Peg100-stearate) and fatty acids such as stearic acid, lauric acid.

The viscosity modifying agents are employed in an amount sufficient to provide the inventive composition with a viscosity such that when the composition is applied to hair, the composition does not easily drip down the hair fibers in a fluid-like manner and it is able to hold the fibers together during the treatment or application period. At the same time, the viscosity of the resulting hair strengthening composition is such that the composition is easy to spread or apply to the hair to be treated in a uniform manner.

Emollients, Fatty Substances (v)

Useful emollients include any of those materials that protect against wetness or irritation or soften, soothe, coat, lubricate, moisturize, protect and/or cleanse the hair. Suitable emollients include one or more silicone compounds, e.g., dimethicones, cyclomethicones, cyclosiloxanes, dimethicone copolyols or mixtures of cyclomethicones and dimethicone/vinyldimethicones, polyols such as sorbitol, glycerine, propylene glycol, ethylene glycol, polyethylene glycol, caprylyl glycol, polypropylene glycol, 1,3-butane diol, hexylene glycol, isoprene glycol, xylitol, ethylhexyl palmitate, triglycerides such as caprylic/capric triglycerides and fatty acid esters such as cetearyl isononanoate and cetyl palmitate.

Suitable fatty substances include hydrocarbon-based oils of animal origin such as perhydrosqualene, hydrocarbon-based plant oils such as liquid triglycerides of fatty acids containing from about 4 to about 10 carbon atoms such as heptanoic or octanoic acid triglycerides, sunflower oil, corn oil, soy bean oil, grapeseed oil, sesame oil, apricot oil, macadamia oil, castor oil, avocado oil, caprylic/capric acid triglycerides, jojoba oil, shea butter; linear or branched hydrocarbons of mineral or synthetic origin, such as liquid paraffins and derivatives thereof, petroleum jelly, polydecenes, hydrogenated polyisobutene; synthetic esters and ethers, in particular fatty acids, such as purcellin oil, isopropyl myristate, 2-ethylhexyl palmitate, 2-octyldodecyl stearate, 2-octyldodecyl emcee, isostearyl isostearate, hydroxylated esters such as isostearyl lactate, octyl hydroxystearate, octyldodecyl hydroxystearate, diisostearyl malate, triisocetyl citrate, fatty alcohol heptanoates, octanoates and decanoates; polyol esters, for instance propylene glycol dioctanoate, neopentyl glycol diheptanoate, diethylene glycol diisononanoate, pentaerythritol esters; fatty alcohols of from about 12 to about 26 carbon atoms, for instance octyldodecanol, 2-butyloctanol, 2-hexyldecanol, 2-undecyl pentadecanol, oleyl alcohol; partially hydrocarbon-based and/or silicone-based fluoro oils; silicone oils, for instance volatile or non-volatile, linear or cyclic polydimethylsiloxanes (PDMS) which are liquid or pasty at ambient temperature (25° C.) such as cyclomethicones, dimethicones, optionally those containing comprising a phenyl group such as phenyl trimethicones, phenyl trimethylsiloxydiphenylsiloxanes, diphenylmethyl-dimethyltrisiloxanes, diphenyl dimethicones, phenyl dimethicones, polymethylphenylsiloxanes, etc., and mixtures thereof.

Preservatives (vi)

Optionally, one or more preservatives may be included in the hair strengthening composition herein. Examples of suitable preservative include glycerine-containing compounds such as glycerine and ethylhexylglycerine, phenoxyethanol, benzyl alcohol, EDTA, potassium sorbate, grapefruit seed extract, and alkyl diols such as propylene glycol and caprylyl glycol.

Skin Protectants (vii)

The hair fiber strengthening composition herein can contain one or more skin protectants, i.e., materials that prevent the transmission of microbes such as antibacterial agents, skin cleansing agents such as disinfectants and antiseptic agents, and sunscreen agents. Suitable skin cleansing agents include sodium cocyl amino acids, benzalkonium chloride and centrimonium chloride.

Penetration Enhancers (viii)

The hair fiber strengthening composition herein can contain organic solvents, surfactants, hydrogen-bonding disrupting agents such as urea to enhance penetration of the $Me^+$ cations into the hair cortex. Nonionic, anionic, amphoteric or cationic surfactants can be used. Silicone surfactants, such as silicone polyether surfactants, trisiloxane surfactants, silicone superspreaders can be used to help both the wetting of hair fibers and penetration of $Me^+$ cations. In particular, hydrolytically stable silicone superspreaders such as Silsoft Spread MAX silicone superspreader available from Momentive Performance Materials Inc. are preferred.

Antioxidants (ix)

Any of the known and conventional antioxidants heretofore incorporated in hair care and other personal care products can be used herein. Suitable antioxidants include sodium sulfite, sodium hydrogen sulfite, ascorbic acid and ascorbate salts.

Hair Colorants

The hair strengthening composition herein can contain hair color or dye numerous kinds of which, both natural and synthetic, are known in the art. The amounts of hair colorants to be included in the hair strengthening composition can vary widely depending on the type of colorant, the hair coloring effects desired and other well known factors. For particular in this regard, reference may be made to Lewis et al., editors, "The Coloration of Wool and Other Keratin Fibres", Chapter 11, "Christie et al., "The Coloration of Human Hair", pp. 229-248 (Wiley, 2013), the contents of which are incorporated by reference herein.

It may be particularly advantageous to include within an organic compound or plant extract which reacts with $Me^+$ cation of the $Me^+(X^-)_n$ compound herein, especially $Fe^{2+}$ and $Fe^{3+}$ cations, to form color. Examples of such color-forming organic compound and plant extract include, but are not limited to, tannic acid, tannins, pyrogalloltannins (geranin tannin) and catechol tannins, gallic acid and derivatives thereof, gallnut, pyrogallol, logwood, hematein, catechol, any of oxybenzones-1 to 9, salicylic acid and derivatives, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, wine extract, wine, tea infusions, fruit juices, berry juices, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, luteolinidin and mixtures thereof.

Of the foregoing color formers, preferred examples include gallic acid and derivatives thereof, oxybenzone-4, salicylic acid and derivatives thereof, ferulic acid, turmeric extract, Scutellaria root extract, and quercetin.

Useful gallic acid derivatives include the alkyl esters of gallic acid, e.g., linear or branched alkyl esters containing from 1 to about 10, and preferably from 2 to about 5, carbon atoms. Specific examples of gallic acid alkyl esters include ethyl gallate, propyl gallate and isoamyl gallate. Gallic acid and derivatives thereof may be chemically synthesized according to known methods isolated from plants or obtained by derivatizing a plant extract. Extracts containing gallic acid or derivative thereof isolated from plants may be directly used. For example, gallic acid derived from *Aralia elata* (Japanese angelica-tree), gallic acid derived from gallnut produced by *Rhus javanica* (nut gall tree), or an extract containing the same may be used. Still further, a derivative obtained by chemically esterifying gallic acid may also be used.

Examples of salicylic acid derivatives include esters and salts of salicylic acid. Examples of the salicylic acid salt include alkali metal salts of salicylic acid, e.g., sodium salicylate. Examples of salicylic acid esters include linear or branched alkyl esters and phenyl esters containing from 1 to about 10 carbon atoms. Specific examples of such salicylic acid esters include octyl salicylate, phenyl salicylate and methyl salicylate.

Auxiliaries (xi)

The hair fiber strengthening composition herein may also comprise one or more auxiliaries such as structurants, waxes, humectants, fragrances, UVA and UVB sunscreen agents such as octylmethoxycinnamate, octocrylene, avobenzone, zinc oxide and titanium oxide, vitamins, panthenol, pearlescent agents, trace elements, sequestering agents, nutrients, anti-hair loss agents, antidandruff agents, propellants, ceramides, polymers, in particular film-forming polymers, styling polymers such as PVP/VA, polyurethane styling polymers, corn starch-derived styling polymers, fillers, nacres, pre-formed colorants, in particular pigments and dyes, in known and customary amounts. The hair fiber strengthening composition can also contain plant and/or animal proteins such as keratin, silk proteins, wheat proteins, pea proteins and soy proteins, hydrolyzed proteins, gelatin, collagen, peptides, amino acids, and the like.

The hair fiber strengthening composition herein can be formulated as a spray, serum, gel, cream, lotion, mousse, or the like. The hair strengthening composition can also be applied to a substrate such as a nonwoven material, a sponge, a cloth, a brush, etc., which can then be used to apply the composition to hair to be strengthened. The hair fiber strengthening composition may be formulated for application to hair as an ultrasonic mist.

D. EXAMPLES

The present invention will be better understood from the examples that follow, all of which are intended for illustrative purposes only and do not limit the scope of the appended claims.

(1) Combined Hair Fiber Strengthening and Thermal Hair Shaping Procedure

A one inch wide commercial ceramic flat iron is mounted on a texture analyzer (Micro Stable) to maintain a constant gliding speed of 15 mm/s and a constant contact force of 2 kg. A hair tress to be treated is held by the clamp of the texture analyzer moving arm. The ironing method utilized is described in detail in *J. Cosmet. Sci.*, 64, 1-13 (2013), the entire contents of which are incorporated by reference herein.

(2) Measurement of Hair Fiber Tensile Strength and Thermal Damage Assessment

The tensile strength of the hair fibers were measured by single fiber tensile tests using a sample of 50 fibers and a Dia-Stron automated tensile tester (Dia-Stron Ltd.). Hair fibers were immersed in water for at least 30 minutes at room temperature for Wet Young's Modulus measurements. Hair fiber strength was determined by measuring Wet Young's Modulus, the results of which correlate well with hair fiber tensile strength.

Application of the hair strengthening composition of the invention to hair that is about to undergo thermal hair shaping will be effective to retain on average a significantly greater Wet Young's Modulus than that of hair that has been thermally shaped by some procedure that is outside the scope of this invention. For example, levels of Wet Young's Modulus of hair fibers that have been treated by the present invention can average from at least about 10, preferably at least about 15 and more preferably at least about 20, percent greater than that of thermally shaped hair resulting from other methods.

Similarly, thermal hair shaping procedures utilizing the hair strengthening composition herein will significantly lower the average reduction in Wet Young's Modulus of the treated hair fibers compared to the average reduction in Wet Young's Modulus of thermally shaped hair fibers resulting from other methods. For example, the average reduction in Wet Young's Modulus of hair fibers treated in accordance with the invention can be about 20, preferably at least about 30 and more preferably at least about 40, percent less than that of hair fibers treated by other methods.

Thermal damage to the hair fibers was determined by measuring the reduction of Wet Young's Modulus of the ironed hair relative to the untreated hair. The percentage reduction of the Wet Young's Modulus is calculated as follows:

Percentage reduction of the Wet Young's Modulus is defined as % $ER=(E_o-E_t)*100/E_o$ where:
$E_o$=Average of the Wet Young's Modulus of the untreated tress before ironing
$E_t$=Average of the Wet Young's Modulus of the ironed tress As the percentage reduction of the Wet Young's Modulus declined, there resulted a corresponding reduction in thermal damage to the hair fibers.

(3) Straightening Efficacy

Following the ironing procedures, the treated tresses were washed with 10 weight percent aqueous sodium lauryl ether sulfate (SLES) solution and dried and stored for 1 hour in a 90% RH chamber. The tresses were hung vertically and measured for length.

Straightening efficacy is defined as % $SE=((L_t-L_o)/(L_s-L_o))\times 100$ where:
$L_t$=length of the straightened hair after 1 hour at 90% RH,
$L_o$=length of the curly unstraightened hair after 1 hour at 90% RH
$L_s$=length of the hair in the straight configuration (maximum length)

A straightening efficiency higher than 50% after a wash and exposure at 1 hour 90% relative humidity indicated that the hair was effectively straightened.

(4) Uptake of Zinc and Iron Cations by the Treated Hair Fibers

The uptake of zinc/iron cations by the treated hair fibers was measured by the ICP-EOS method (Ozden et al., Clinical Biochemistry 45 (2012) 753). The hair sample was digested in a microwave by adding an acid mixture of 14 ml $HNO_3$ and 4 ml $H_2O_2$ to a 0.3 g hair sample. The samples were allowed to react for 3 minutes. The digested material was diluted to 50 ml and analyzed by ICP-EOS (Perkin Elmer, Optima 5300 dv). Since each hair sample has an intrinsic zinc or iron content before treatment, each hair sample was analyzed before and after treatment with aqueous hair treatment composition. The metal uptake as reported in the examples was the difference between the metal level before treatment and the metal level after the treatment.

Examples 1-6 and Comparative Examples 1-3:
High pH $Zinc^{2+}$ Hair Fiber Treatment Compositions for Thermal Hair Shaping In all of the tables herein, amounts of components of the various treatment compositions are in weight percent.

The hair fiber treatment compositions of Table 2 below were prepared by dissolving the salts in water and adjusting the pH by addition of 10 weight % aqueous NaOH. The compositions of Examples 2-6 and Comparative Examples 2 and 3 were prepared by mixing a 10 weight % solution of maltobionic acid and a concentrated solution of zinc chloride or zinc acetate followed by adjusting the pH with 10 weight % aqueous NaOH or tris(tromethamine) to obtain the listed hair fiber treatment compositions. The hair fiber treatment compositions of the invention were clear and stable for at least 40 days at pH 8 whereas the comparison hair fiber treatment compositions were unstable forming two phases.

TABLE 2

Zinc-Containing Hair Fiber Treatment Compositions

| Component (wt %) | Ex. 1 | Ex. 2 | Ex. 3 | Ex. 4 | Ex. 5 | Ex. 6 | Comp. Ex. 1 | Comp. Ex. 2 | Comp. Ex. 3 |
|---|---|---|---|---|---|---|---|---|---|
| zinc glucoheptonate | 6.5 | | | | | | | | |
| zinc chloride | | 1.13 | 1.13 | 1.13 | | | | | 1.13 |
| zinc acetate dihydrate | | | | | 1.82 | 1.82 | 6.5 | 1.82 | |
| maltobionic acid | | 5.96 | 4.46 | 5.96 | 5.96 | 4.47 | | 2.98 | 2.98 |
| sodium hydroxide (to adjust pH) | 0.73 | 1.1 | 1.5 | | 1.14 | 1 | q.s to pH 8 | 0.9 | 0.98 |
| tris(tromethamine) | | | | 6.5 | | | | | |
| water | 92.77 | 91.81 | 91.4 | 86.42 | 91.08 | 92.71 | q.s to 100 | 94.3 | 94.91 |
| pH | 8 | 8 | 8 | 8 | 8 | 8 | 8 | 8 | 8 |
| mole ratio —O—C(O)—R to Zn | 2 | 2 | 1.5 | 2 | 2 | 1.5 | NA | 1 | 1 |
| solution appearance | clear, stable | clear, stable | clear, stable | clear, stable | clear, stable | clear, stable | 2 phases, unstable | 2 phases, unstable | 2 phases, unstable |

The results summarized above in Table 2 also demonstrate the importance for a mole ratio of oxidized carbohydrate anion to $M_n$ cation, illustrated for maltobionate anion and Zn cation, of greater than 1.0. Thus below this mole ratio (Comparative Examples 2 and 3), the hair fiber treatment compositions were unstable and therefore unsuitable for use as hair strengthening compositions.

Examples 7-8 and Comparative Examples 4-9:
Straightening of Natural Curly Hair

Natural curly hair tresses (2 g) were obtained from International Hair Importers, Glendale, N.Y. Hair fiber treatment compositions containing zinc maltobionate were prepared as in Example 2 of Table 2.

The curly hair tresses of Examples 7-8 and Comparative Examples 4-9 of Table 3 below were immersed in 50 ml of the aqueous compositions described therein for 30 minutes at room temperature. Excess liquid was removed by squeezing a tress between the fingers. Each tress was blow-dried, steamed with a handheld clothing steamer for 30 seconds, ironed for 3 passes with a flat iron at 234° C., steamed again for 30 seconds and ironed for another 3 passes in order to provide a straightened, relaxed hair tress. The hair tresses were then washed with 10 weight % aqueous SLES and dried.

for another 3 passes in order to provide a straightened relaxed hair tress. Each hair tress was then washed with 10 weight percent aqueous SLES, dried and steam-ironed for another cycle.

TABLE 3

Straightening and Tensile Strength of Hair Fibers Ironed at T >200° C.

| Components of Hair Wetting Composition (wt %) | Ex. 7 | Ex. 8 | Ex. 9 | Comp Ex. 4 | Comp Ex. 5 | Comp Ex. 6 | Comp Ex. 7 | Comp. Ex. 8 |
|---|---|---|---|---|---|---|---|---|
| zinc chloride | 1.14 | 1.14 | 1.14 | 1.14 | 1.14 | 0 | 0 | 0 |
| maltobionic acid | 5.96 | 5.96 | 5.96 | 5.96 | 5.96 | 0 | 0 | 0 |
| zinc acetate | | | | | | | 1.6 | 6.5 |
| Gafquat 734[1] | | | | | | | 5 | |
| Silsoft SME253[2] | | | | | | | | 1.7 |
| NaOH | 0.95 | 1.1 | 0.5 | 0.15 | 0.45 | 0 | q.s to pH 8 | q.s to pH 8 |
| water | q.s to 100 | q.s to 100 | q.s to 100 | q.s to 100 | q.s to 100 | 100 | q.s to 100 | 100 |
| pH | 8 | 10 | 6 | 2 | 4 | 6 | 8 | 8 |
| white residue during ironing | no | no | no | no | no | no | yes | yes |
| Wet Young's Modulus[3] ($\times 10^9$ Pa) | 1.64 | 1.45 | 1.61 | 1.33 | 1.39 | 1.09 | 0.95 | 1.39 |
| % Straightening Efficiency | 86 | 77 | 55 | 55 | 61 | 77 | — | — |
| % Reduction of Wet Young's Modulus | 18 | 28 | 19 | 34 | 31 | 46 | 53 | 46 |
| zinc uptake (ppm) | 680 | 289 | 793 | 491 | 578 | 0 | — | — |

[1]Gafquat 734 is a quaternary copolymer of vinylpyrrolidone.
[2]Silsoft SME253, an aminosilicone emulsion, is available from Momentive Performance Materials Inc.
[3]The average value of Wet Young's Modulus of untreated curly hair before ironing is $2.10^9$ Pa.

The thermally treated tresses of Examples 7-9 Ln Table 3 show that treatment with $Zn^{+2}$ maltobionate resulted in significantly higher average retention of Wet Young's Modulus compared to that of Comparative Examples 4 to 8, i.e., 1.57 average Wet Young's Modulus for Comparative Examples 4 to 8. Data in Table 3 also show that the thermally treated hair of Examples 7 to 9 underwent an average percent reduction of Wet Young's Modulus, i.e., 21.7 percent, that was considerably lower than the 42 percent reduction of Wet Young's Modulus of Comparative Examples 4 to 8.

Comparative Example 7 is a repeat of Example 2 of U.S. Pat. No. 3,958,581. After the treated hair tress was ironed, it had become very tacky and exhibited large amounts of a white residue making the treatment impractical for thermal shaping. Comparative Example 8 is a pH 8 composition containing a zinc acetate salt in place of zinc carbohydrate salt and an aminosilicone. This hair treatment composition also produced a large amount of white residue and weakened the hair significantly.

Example 10 and Comparative Example 9: Straightening of Bleached Curly Hair

Hair Shaping Method of Example 9

Four Latin curly hair tresses (2 g) (International Hair Importers, Glendale, N.Y.) were bleached with a commercial bleach according to the protocol prescribed by the product manufacturer. The tresses were rinsed, washed and blow-dried.

A solution of 4.2% zinc glucoheptonate (ISALTIS, Lyon, France) at pH 8 was prepared as in Example 1.

Each bleached curly hair tress was immersed in 50 ml of the zinc glucoheptonate hair strengthening solution for 30 min at room temperature (25° C.). Excess liquid was removed by squeezing a tress between the fingers. Following blow-drying, each tress was steamed with a handheld clothing steamer for 30 second, ironed for 3 passes with a flat iron at 234° C., steamed again for 30 seconds and ironed Hair Shaping Method of Comparative Example 9

The tresses of Comparative Example 9 were prepared by immersion in 50 ml of water in the absence of zinc glucoheptonate for 30 min at room temperature (25° C.). Each tress was then subjected to the same process steps and ironing as described for the tress of Example 9

Tensile Properties of the Shaped Hair Tresses.

The hair tresses of Example 10 and Comparative Example 90 were left for 24 h at rest, washed with a 10 weight percent aqueous SLES solution and blow-dried before measurement of their tensile properties, the results of which are set forth in Table 4 as follows:

TABLE 4

Tensile Properties of Ironed Bleached Hair Fibers

| Components (wt %) | Ex. 10 | Comp. Ex. 9 |
|---|---|---|
| Zinc Glucoheptonate | 4.2 | 0 |
| NaOH | 0.47 | 0 |
| water | 95.33 | 100 |
| % Reduction of Wet Young Modulus | 57 | 86 |

The zinc glucoheptonate hair fiber treatment composition (Example 10) appreciably reduced the thermal damage to the hair compared with the hair treated with water only (Comparative Example 9).

Examples 11-17: Enhanced Zinc and Iron Uptake within the Hair Cortex

Natural curly hair tresses (2 g) (International Hair Importers, Glendale, N.Y.) were immersed in 50 ml of the metal solutions shown in Table 5 below prepared as in Example 1 for 2 min or 30 min at room temperature. Excess liquid was removed by squeezing a tress between the fingers. Each tress was blow-dried, steamed with a handheld clothing steamer for 30 second, ironed for 3 passes with a flat iron at 234° C., steamed again for 30 seconds and ironed for another 3 passes in order to provide straightened relaxed hair. Each hair tress was then washed with a 10 weight percent aqueous SLES, and dried. The hair metal content was analyzed after the wash and drying cycle.

TABLE 5

Hair Shaping Compositions

| Components (wt %) | Ex. 11 | Ex. 12 | Ex. 13 | Ex. 14 | Ex. 15 | Ex. 16 | Ex. 17 |
|---|---|---|---|---|---|---|---|
| $Zn^{+2}$ maltobionate | 4.5 | 4.5 | 4.5 | 4.5 | | | 3.75 |
| $Fe^{3+}$ maltobionate | | | | | 4.5 | 4.5 | 3.75 |
| NAOH 10% | q.s to pH 8 | q.s to pH 8 | q.s to pH 8 | q.s to pH 8 | q.s to pH 8 | q.s to pH 8 | q.s to pH 8 |
| Silsoft Spread MAX fluid | 0 | 0.5 | 0 | 0.5 | 0 | 0.5 | 0 |
| water | q.s to 100 | q.s to 100 | q.s to 100 | q.s to 100 | q.s to 100 | q.s to 100 | |
| contact time (min) | 2 | 2 | 30 | 30 | 30 | 30 | 30 |
| $Zn^{+2}$ uptake (ppm) | 373 | 555 | 407 | 638 | 0 | 0 | 475 |
| $Fe^{3+}$ uptake (ppm) | 0 | 0 | 0 | 0 | 19 | 26 | 20 |

The $Fe^{3+}$ maltobionate salt in Table 5 was prepared by combining ferric chloride with maltobionic acid in water and adjusting the pH with 50 NaOH in a manner similar to the preparation described in Example 2.

As shown by data in Table 5 above, the hair tresses treated with the metal solution containing Silsoft Spread Max (Ex. 12, 14 and 16) exhibited higher metal uptake than the compositions which omitted the silicone superspreaders.

Examples 18-31: Hair Fiber Treatment Compositions

The following compositions illustrate various hair fiber treatment compositions formulated with hair strengthening agents in accordance with the invention.

Examples 18-21: Hair Lotion

Hair fiber strengthening compositions were formulated as hair lotions/hair conditioners with the components and amounts thereof indicated in Table 6 below:

TABLE 6

Hair Lotions/Hair Conditioners

| Components (wt %) | Ex. 18 | Ex. 19 | Ex. 20 | Ex. 21 |
|---|---|---|---|---|
| Ceteareth-20 and Cetearyl alcohol | 5.5 | | | 5.5 |
| Cellulose (Methocel) | | 2 | 1 | |
| Coconut oil | 5 | | | |
| $Zn^{2+}$ glucoheptonate | 3 | 3 | | |
| $Zn^{2+}$ maltobionate | | | 5 | 6.5 |
| Silsoft EMU160-A emulsion | 1.67 | 1.67 | 1.67 | 1.67 |
| NaOH | q.s to pH 8 | 0.33 | q.s to pH 8 | q.s to pH 8 |
| Preserving agent | 0.5 | 0.5 | 0.5 | 0.5 |
| Fragrance | 0.4 | 0.4 | 0.4 | 0.4 |
| Water | q.s to 100 | q.s to 100 | q.s to 100 | q.s to 100 |
| pH | 8 | 8 | 8 | 8 |

Silsoft EMU160-A is a silicone emulsion of dimethiconol (Momentive Performance Materials, Inc.)

The hair lotions/hair conditioners of Table 6 can be utilized as leave-in or rinse-off treatments.

Examples 21-23: Hair Serum Compositions

Hair fiber strengthening compositions were formulated as hair serums with the components and amounts thereof indicated in Table 7 below:

TABLE 7

Hair Serums

| Components (wt %) | Ex. 22 | Ex. 23 |
|---|---|---|
| sodium carboxymethylcellulose (Cekol CMC 2000) | 1.25 | 1.25 |
| Silsoft Spread MAX silicone superspreader | 0.5 | |
| Genapol X-050 wetting agent | | 0.5 |
| $Zn^{2+}$ maltobionate | 6.5 | 6.5 |
| Silsoft EMU160-A silicone emulsion | 1 | 1 |
| NaOH | 1.1 | 1.1 |
| panthenol | 1 | |
| preservative | 0.5 | 0.5 |
| fragrance | 0.4 | 0.4 |
| water | q.s to 100 | q.s to 100 |
| pH | 8 | 8 |

Genapol X-050, an iso tridecyl alcohol polyglycol ether with 5 EO units available from Clariant The hair serums of Examples 22-23 of Table 7 can be utilized as leave-in or rinse-off hair treatments.

Examples 24-26: Hair Spray Compositions

Hair fiber strengthening compositions were formulated as hair sprays with the components and amounts indicated in Table 8 below:

TABLE 8

Hair Sprays

| Components (wt %) | Ex. 24 | Ex. 25 | Ex. 26 |
|---|---|---|---|
| sodium carboxymethylcellulose cekol CMC 2000 | | 0.5 | 0.5 |
| Silsoft Spread MAX silicone superspreader | | 0.5 | |
| Genapol X-050 wetting agent | 0.5 | | 0.5 |
| $Zn^{2+}$ glucoheptonate | | | |
| $Zn^{2+}$ maltobionate | 6.5 | 6.5 | 6.5 |
| amino acid blends | 1 | 1 | 1.67 |
| glycerine | 2 | 2 | 2 |
| fragrance | 0.4 | 0.4 | 0.4 |
| preservative | 0.5 | 0.5 | 0.5 |
| NaOH | q.s to pH 8 | q.s to pH 8 | q.s to pH 8 |
| water | q.s to 100 | q.s to 100 | q.s to 100 |
| pH | 8 | 8 | 8 |

Examples 27-28: Hair Shampoo Compositions

Hair fiber strengthening compositions were formulated as hair shampoos with the components and amounts thereof indicated in Table 9 below:

TABLE 9

Hair Shampoos

| Components (wt %) | Ex. 27 | Ex. 28 |
|---|---|---|
| magnesium aluminum silicate | 0.5 | |
| ammonium lauryl sulfate | 12 | |
| alkyl glucoside blend | | 12 |
| coco glucoside | | 0.5 |
| glyceryl oleate | | 1.2 |
| hydroxyethylcellulose | | 2.5 |
| PPG-ceteth-10 phosphate | 1.8 | |
| $Zn^{2+}$ maltobionate | 4 | 6.5 |
| aloe vera extract | 0.5 | 0.5 |
| panthenol | 0.5 | 0.5 |
| preservative | 0.5 | 0.5 |
| NaOH | q.s to pH 7.5 | q.s to pH 8 |
| water | q.s to pH 100 | q.s to 100 |

Examples 29-31: Hair Mask Compositions

Hair fiber strengthening compositions were formulated as hair masks with the components and amounts thereof indicated in Table 10 below:

TABLE 10

Hair Masks

| Components (wt %) | Ex. 29 | Ex. 30 | Ex. 31 |
|---|---|---|---|
| Ceteareth-20 and Cetearyl alcohol (wt %) | 5.5 | 5.5 | 5 |
| magnesium aluminum silicate | 1 | 1 | 2 |
| Shea butter | 5 | | 1 |
| hydrolyzed silk protein | | | 1 |
| panthenol | | 1 | |
| $Zn^{2+}$ glucoheptonate | 10 | | |
| $Zn^{2+}$ maltobionate | | 6.5 | 10 |
| Silsoft EMU160-A silicone | 1.67 | 1.67 | |
| NaOH | q.s to pH 8 | q.s to pH 8 | q.s to pH 7.5 |
| preservative | 0.5 | 0.5 | 0.5 |
| water | q.s to pH 100 | q.s to 100 | q.s to 100 |
| pH | 8 | 8 | 7.5 |

Example 32 and Comparative Example 10: $Fe^{2+}$ Hair Fiber Strengthening Compositions for Treating Bleached Hair or Dyed Hair Hair treatment compositions were prepared with the components and amounts thereof indicated in Table 11 below:

TABLE 11

$Fe^{2+}$ Hair Fiber Treatment Compositions

| Components (wt %) | Ex. 32 | Comp. Ex. 10 |
|---|---|---|
| ferrous sulfate | 2.1 | 2.1 |
| maltobionic acid | 5 | |
| tromethamine | 0.6 | |
| HCl | 0.2 | |
| NaOH 10% | q.s to pH 8 | q.s to pH 8 |
| water | q.s to 100 | q.s to 100 |
| solution appearance | Clear; stable | 2 phases; unstable |

Platinum bleached tresses (4 g) (International Hair Importers, Glendale, N.Y.) were treated with 1 g of the hair treatment composition of Example 32. Each tress was soaked for 10 min, rinsed with tap water for 30 sec and dried. The hair was shampooed once with 10% SLES solution and dried. The wet tensile properties were measured before and after treatment. The Wet Young's Modulus of platinum dyed hair before treatment was $8.63 \cdot 10^8$ Pa. After the treatment (metal treatment+ shampoo), the Wet Young's Modulus was $1.14 \cdot 10^9$ Pa. The Wet Young's Modulus increase of 32% indicated that the treated hair was considerably strengthened by the metal treatment.

The composition of Example 32 can also be used with $Fe^{2+}$-reactive color formers, e.g., gallic acid/derivatives as previously described, to strengthen and at the same time color the hair being treated. A shampoo containing 14 wt % sodium laureth sulfate, 2% cocobetaine, 1.5% sodium chloride, 1.5% tannic acid (Tannal from Ajinomoto) in water is prepared. The bleached hair is shampooed with the tannic acid shampoo. The tress is soaked with the shampoo for 5 min and rinsed. After rinsing, the composition of Example 32 is applied to the hair and left on the hair for 10 min. The hair is rinsed with warm tap water. The hair become colored with a light brown color. The light brown color is wash resistant.

Other brown color shades can be obtained by treating the hair with natural tannin solutions such as an infusion of Lipton tea or red wine and subsequently developing the color with the composition of Example 32.

Comparative Example 10 demonstrates the instability of an iron cation-containing salt, specifically ferrous sulfate at pH 8. On standing, the hair fiber treatment composition separated into two phases rendering it unsuitable for use in hair strengthening method of the invention. As note above in the case of such a compound, in order to function as a hair fiber strengthening agent, the iron salt should be prepared and maintained at acid pH and only adjusted with base to within a pH of about 6 to about 12 just prior to being contacted with hair to be strengthened. Examples 34-35 and Comparative Example 11: Shaping Method (Straightening) Applied To Bleached Curly Hair With Low pH Treatment Compositions.

Natural curly hair tresses (Hair International importers). were bleached once with a commercial bleach, rinsed, washed and dried before carrying out straightening treatments.

Hair Wetting Metal Solution with pH Less than 7 (Step (a))

The aqueous solutions of Table 12 were prepared by dissolving 0.65 g $Me^+(X^-)_n$ salt in dionized water to obtain a 100 g solution.

pH 8 Buffered Silicone Dispersion Applied after Step (b)

A pH 8 buffer solution was composed of 0.68 g $KH_2PO_4$, 0.19 g of NaOH and 99.13 g dionized water. The silicone emulsion Silsoft AX-E was diluted in the pH 8 buffer to obtain a silicone polymer concentration of 0.3%. Silsoft AX-E is an emulsion of an alkyl aminosilicone sold by Momentive Performance Materials.

Contacting of the Hair Fibers with the Hair Fiber Strengthening Compositions (Steps a-b)

The example hair tress was immersed in the 0.65% metal solution for 30 min at room temperature. Then, the tress was immersed in the pH 8 buffered silicone treatment for 2 min. The hair was blow dried. The comparative tress (Comp Ex. 11) was only immersed in the pH 8 buffered silicone treatment for 2 min and was blow dried.

Thermally Shaping the Hair (Step c)

Once dried, the hair was exposed to steam produced by a steamer home appliance for 1 min. The flat iron plate temperature was 234° C. The tress was ironed 3 passes, exposed to steam for 1 min, turned 90°, clamped and ironed 3 additional passes. After the ironing cycle, the hair tress rested for 48 hours, then was washed with 10% SLES solution and dried. Another identical ironing cycle was performed without reapplying the treatments 1 or 2. After 48 hours, the tresses were washed with 10% SLEs and dried.

TABLE 12

Tensile Properties of Treated Hair Fibers

| Example | Me$^+$ (X$^-$)$_a$ Compound | % Reduction of the Wet Young's Modulus | Straightening Efficiency |
|---|---|---|---|
| Ex. 34 | Zinc Chloride | 38 | + |
| Ex. 35 | Zinc Sulfate | 32 | + |
| Comp. Ex. 11 | None | 66 | + |

The data in Table 12 show that the loss of Wet Young's Modulus during the thermal treatment was significantly reduced by the treatments with Zn$^{2+}$ chloride and Zn$^{2+}$ sulfate salts compared to the Comparative Example 11 which was not treated with the soluble Zn$^{2+}$ salts.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

The invention claimed is:

1. A hair fiber strengthening composition which comprises an aqueous vehicle and a hair strengthening agent which is at least one metal compound of the general formula:

Me$^+$(X$^-$)$_n$ wherein Me$^+$ is the cation of a metal having a valence equal to subscript n, subscript n is 2 or 3 and each X$^-$ independently is an anion of (i) an oxidized carbohydrate of the formula:

$^-$O—C(O)—R wherein R is the residue of the same or different carbohydrate, or an anion (ii) derived from the same or different inorganic or organic acid, provided, there is at least one anion (i), wherein the mole ratio of $^-$O—C(O)—R anions to Me cations is from above about 1.0 to about 2.0, and wherein the composition having a pH of from about 6 to about 11.

2. The hair fiber strengthening composition of claim 1 wherein metal compound Me$^+$(X$^-$)$_n$ is at least one member selected from the group consisting of:

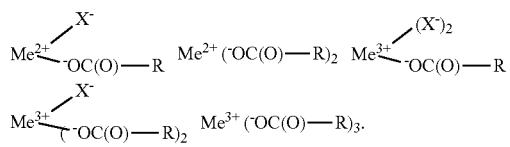

3. The hair fiber strengthening composition of claim 1 wherein the aqueous vehicle is a solution, dispersion or suspension containing the at least one hair fiber strengthening agent.

4. The hair fiber strengthening composition of claim 1 having a pH of from about 7 to about 10.

5. The hair fiber strengthening composition of claim 1 having a pH of from about 8 to about 9.

6. The hair fiber strengthening composition of claim 1 wherein the Me$^+$ is one or more of Fe$^{2+}$, Fe$^{3+}$, Zn$^{+2}$, Mg$^{2+}$, Al$^{3+}$, Cu$^{2+}$, and Cu$^{3+}$ cations.

7. The hair fiber strengthening composition of claim 1 wherein in the $^-$O—C(O)—R anion, each R independently is the residue of the same or different carbohydrate selected from the group consisting of monosaccharides, disaccharides, oligosaccharides and polysaccharides.

8. The hair fiber strengthening composition of claim 1 wherein each $^-$O—C(O)—R anion is independently selected from the group consisting of anions of ribonic acid; ribulonic acid; arabinonic acid; xylonic acid; xylulonic acid; lyxonic acid; allonic acid; altronic acid; gluconic acid; mannonic acid; gulonic acid; idonic acid; galactonic acid; talonic acid; glucoheptonic acid; psiconic acid; fructonic acid; sorbonic acid; tagatonic acid; lactobionic acid; maltobionic acid; isomaltobionic acid; cellobionic acid; oxidized malto-oligosaccharide; oxidized cello-oligosaccharide; oxidized cellulose; chitin; gum arabic; gum karaya; gum xanthan; oxidized gum guar; oxidized locust bean gum; oxidized agars; oxidized algins; and oxidized gellan gum.

9. The hair fiber strengthening composition of claim 1 wherein the mole ratio of $^-$O—C(O)—R anions to Me cations is from above about 1.2 to about 1.8.

10. The hair fiber strengthening composition of claim 1 wherein each X$^-$ anion is independently selected from the group consisting of chloride, fluoride, sulfate, alkylsulfonate, arylsulfonate, alkarylsulfonate, phosphate, oxalate, acetate, citrate and lactate.

11. The hair fiber strengthening composition of claim 1 wherein the total mole concentration of Me$^+$ cations in the composition is from about 0.01 to about 2.

12. The hair fiber strengthening composition of claim 1 wherein the total mole concentration of Me$^+$ cations in the composition is from about 0.1 to about 1.0.

13. The hair fiber strengthening composition of claim 1 wherein the total mole concentration of Me$^+$ cations in the composition is from about 0.2 to about 0.5.

14. The hair fiber strengthening composition of claim 1 wherein metal compound Me$^-$(X$^-$)$_n$, is at least one member selected from the group consisting of Fe$^{2+}$ lactobionate, Fe$^{2+}$ maltobionate, Fe$^{2+}$ isomaltobionate, Fe$^{3+}$ lactobionate, Fe$^{3+}$ maltobionate, Fe$^{3+}$ isomaltobionate, Fe$^{2+}$ gluconate, Fe$^{3+}$ gluconate, Fe$^{2+}$ glucoheptonate, Fe$^{3+}$ glucoheptonate, Zn$^{2+}$ lactobionate, Zn$^{2+}$ maltobionate, Zn$^{3+}$ isomaltobionate, Zn$^{2+}$ gluconate, Zn$^{2+}$ gluconate, Zn$^{2+}$ glycerophosphate, Mg$^{2+}$ maltobionate, Mg$^{2+}$ isomaltobionate, Mg$^{2+}$ gluconate, Mg$^{2+}$ glucoheptonate, Al$^{3+}$ maltobionate, Al$^{3+}$ isomaltobionate, Al$^{3+}$ gluconate, Al$^{3+}$ glucoheptonate, Cu$^{2+}$ maltobionate, Cu$^{2+}$ isomaltobionate, Cu$^{2+}$ gluconate, Cu$^{2+}$ glucoheptonate, Cu$^{3+}$ maltobionate, Cu$^{3+}$ isomaltobionate, Cu$^{3+}$ gluconate and Cu$^{3+}$ glucoheptonate.

15. The hair fiber strengthening composition of claim 2 wherein each Me$^+$ cation is independently selected from the group consisting of Fe$^{2+}$, Fe$^{3+}$, Zn$^{3+}$, Mg$^{2+}$, Mg$^{3+}$, Al$^{3+}$ and Cu$^{2+}$, each acid-derived anion is independently selected from the group consisting of chloride, fluoride, sulfate, alkysulfonate, aryl sulfonate, alkarylsulfonate, phosphate, oxatate, acetate, citrate and lactate, and each $^-$OC(O)—R anion is independently selected from the group consisting of lactobionate, maltobionate, isomaltobionate, gluconate and glucoheptonate.

16. The hair fiber strengthening composition of claim 1 wherein the mole ratio of $^-$O—C(O)—R anion to anion derived from an inorganic or organic acid is from about 0.1 to about 15, the composition containing from about 1 to about 20 weight percent $Me^+(X^-)_n$ compound.

17. The hair fiber strengthening composition of claim 15 further comprising at least one metal compound selected from the group consisting of $Fe^{2+}$ chloride, $Fe^{2+}$ fluoride, $Mg^{2+}$ chloride, $Fe^{3+}$ chloride, $Fe^{2+}$ sulfate, $Fe^{3+}$ sulfate, $Mg^{+2}$ sulfate, $Fe^{2+}$ phosphate, $Fe^{3+}$ phosphate, $Mg^{+2}$ phosphate, $Fe^{2+}$ oxalate, $Fe^{3+}$ oxalate, $Fe^{2+}$ acetate, $Fe^{3+}$ acetate, $Fe^{2+}$ glycerophosphate, $Fe^{3+}$ glycerophosphate, $Zn^{2+}$ chloride, $Zn^{2+}$ fluoride, $Zn^{+2}$ sulfate, $Zn^{2+}$ phosphate, $Zn^{2+}$ acetate, $Zn^{2+}$ aspartate, $Zn^{2+}$ citrate, $Zn^{2+}$ lactate, $Zn^{2+}$ malate, $Zn^{2+}$ glycerophosphate, $Fe^{2+}$ glycinate, $Mg^{+2}$ aspartate, $Mg^{+2}$ citrate nonahydrate, $Mg^{+2}$ gluconate, $Mg^{+2}$ lactate, $Mg^{+2}$ glycerophosphate, $Mg^{+2}$ malate, $Mg^{2+}$ glycinate, $Al^{3+}$ sulfate, $Al^{3+}$ chloride and $Cu^{2+}$ sulfate.

18. The hair fiber strengthening composition of claim 1 comprising at least one $Me^+$ cation-reactive color former.

19. The hair fiber strengthening composition of claim 18 wherein the $Me^+$ cation is $Fe^{2+}$ or $Fe^{3+}$ and the color former is gallic acid or gallic acid derivative.

20. The hair fiber strengthening composition of claim 1 comprising at least one additional component selected from the group consisting of silicone-based hair conditioning agent, organic diluent/solvent, surfactant/emulsifier, viscosity modifier, emollient, fatty substance, preservative, skin protectant, penetration enhancer, antioxidant, fragrance, colorant, $Me^+$ cation-reactive color former, plant extract, nutrient and auxiliary agent.

21. The hair fiber strengthening composition of claim 1 wherein formaldehyde and/or formaldehyde precursor is substantially absent.

22. The hair fiber strengthening composition of claim 1, wherein the metal compound is present in an amount of from about 0.1 to about 80 weight percent.

23. The hair fiber strengthening composition of claim 1, wherein the metal compound is present in an amount of from about 1 to about 60 weight percent.

24. The hair fiber strengthening composition of claim 1, wherein the metal compound is present in an amount of from about 5 to about 40 weight percent.

* * * * *